United States Patent [19]

Grant et al.

[11] 4,361,574
[45] Nov. 30, 1982

[54] INHIBITORS OF MAMMALIAN COLLAGENASE

[75] Inventors: Norman H. Grant, Wynnewood; Donald E. Clark, Norristown, both of Pa.

[73] Assignee: American Home Products Corporation, New York, N.Y.

[21] Appl. No.: 307,710

[22] Filed: Oct. 2, 1981

[51] Int. Cl.$^3$ .......................................... A61K 31/425
[52] U.S. Cl. .................................................. 424/270
[58] Field of Search ......................................... 424/270

[56] References Cited

U.S. PATENT DOCUMENTS 4,214,089  7/1980  Fenichel et al. ..................... 424/270

*Primary Examiner*—Stanley J. Friedman
*Attorney, Agent, or Firm*—George Tarnowski

[57] ABSTRACT

A method of inhibiting mammalian collagenase by using 3-(p-substituted phenyl)-thiazolo[3,2-a]benzimidazole-2-alkanoic acids and esters thereof, and the pharmaceutically acceptable salts thereof.

7 Claims, No Drawings

INHIBITORS OF MAMMALIAN COLLAGENASE

BACKGROUND OF THE INVENTION

Collagen is the major organic component of the surface tissue found in the cornea, skin, gastro-intestinal viscera, joint mucosa and other areas of the body. The collagen molecule has a molecular weight of 300,000, and is composed of three helical polypeptide chains which are wound around a common axis forming a coiled chain. In solution collagen molecules exist as long rods about 3000×15 A, but at a temperature of 37° C. and a pH of 7, the molecules polymerize into insoluble fibrils. Thus, it is as fibrils that collagen invariably exists in tissue. The helical structure of undenatured collagen is remarkably resistant to attack by proteolytic enzymes; however, there have been discovered a number of natural enzymes, i.e., animal collagenases, which are capable of breaking down collagen by cleaving the collagen molecule across the helical backbone yielding ¾ and ¼ length fragments.

The relationship between collagenase and the destruction of collagen-based tissue has been found in a number of disease states affecting various parts of the body, all of which are basically similar in that collagen constitutes the major organic component, e.g., skin, cornea, gastro-intestinal viscera, joint mucosa, etc. For example, in connection with corneal tissue, it has been shown that collagenase is responsible for ulcers appearing after the eye has been burned with alkali. Similarly, the relationship exists for other ulcerous conditions of the cornea such as viral ulcers, e.g., herpes simplex, vaccinia, etc.; bacterial ulcers, e.g. Pseudomonas, etc.; degenerative ulcers and ulcers of unknown origin, e.g., associated with rheumatoid arthritis, Mooren's ulcer, furrow ulcer; and ulcers secondary to drying, e.g., erythema multiforme (Stevens-Johnson Syndrome).

In mammals, collagenase is one of the key enzymes involved in the cartilage and joint destruction of rheumatoid arthritis; see, for example, *Arthritis and Rheumatism*, 20 (6): 1231 (1977). The action of mammalian collagenase has also been implicated as a causative factor in several other diseases in mammals. These diseases include periodontal disease, tumor invasiveness, and epidermolysis bullosa; see, for example, *American Journal of Pathology*, 92 (2): 509 (1978) and *The New England Journal of Medicine*, 291 (13): 652 (1974).

Accordingly, collagenase inhibitors can be advantageously used to block pathologies in which destruction of collagenous connective tissue plays a central role, such as for example, periodontal disease, rheumatoid arthritis, corneal ulcerations, and so forth.

DESCRIPTION OF THE INVENTION

The present invention is directed to a method of inhibiting mammalian collagenase in mammals afflicted with a disease state in which collagen is broken down by collagenase which comprises administering to such an afflicted mammal an amount sufficient to reverse said collagenase-induced collagen breakdown of a collagenase inhibitor having the formula:

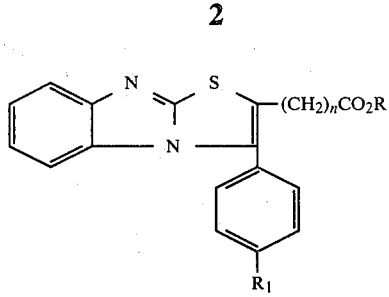

wherein R is hydrogen or lower alkyl, $R_1$ is hydrogen, lower alkyl, lower alkoxy, trifluoromethyl or halo, n is 1 or 2 and pharmaceutically acceptable salts thereof.

The compounds of formula I and their method of preparation are disclosed in U.S. Pat. Nos. 4,214,089, and 3,704,239.

The term pharmaceutically acceptable salts includes the salts pharmacologically-acceptable organic and inorganic acids such as hydrochloric, hydrobromic, sulfuric, nitric, phosphoric, methanesulfonic, benzenesulfonic and the like, alkali metal carboxylates and carboxylates of a pharmacologically acceptable cation derived from ammonia or a basic amine.

The alkali metal carboxylates of the invention can be prepared by mixing stoichiometrically equivalent amounts of the free acids, preferably in aqueous solution, with wolutions of alkali metal bases, such as sodium potassium, and the lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The terms "lower alkyl" and "lower alkoxy" when used herein and in the appended claims includes straight and branched chain hydrocarbon radicals and moieties having from 1 to about 6 carbon atoms, illustrative members of which are methyl, ethyl, n-propyl, i-propyl, n-butyl, t-butyl, n-pentyl, n-hexyl, 3-methylpentyl, 2,3-dimethylbutyl, and the like.

"Alkali metal" includes, for example, sodium potassium lithium, and like. "Halo" includes fluoro, chloro, bromo and iodo. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

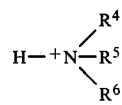

wherein $R^4$, $R_5$, and $R^6$, independently, are hydrogen, alkyl of from about 1 to about 6 carbon atoms, cycloalkyl of from about 3 to about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or when taken together with the nitrogen atom to which they are attached, any two of $R^4$, $R^5$, and $R^6$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinum, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)-methylammonium, phenylmonoethanolammonium, and the like.

The term "pharmacologically acceptable carrier" contemplates usual and customary substances employed to formulate solid, oral unit dosages for pharmacological purposes, including in its broadest form animal feedstuff. It also includes those employed to formulate either in unit dose or multi dose form, oral and injectable suspensions and solutions, either directly or for reconstitution before administration.

To formulate dosages for administration according to this invention the compounds of formula I can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacarthy, methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases the proportion of active ingredients in said compositions both solid and liquid will be at least sufficient to impart collagenase inhibitory activity thereto on oral or parenteral administration.

In practicing the method of the invention, the instant compositions can be administered to warm-blooded animals, e.g., mice rats, rabbits, dogs, horses, monkeys, anthropoid apes, and the like, in a variety of dosage forms, alone or in combination with pharmacologically effective carriers, preferably orally or by injection.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the tangible embodiments of the invention are most desirably administered at a concentration level that will generally afford effective results without causing any harmful or deleterious side effects.

The ability of the compounds of the invention to inhibit collagenase is demonstrated by testing in an enzyme assay using collagenase produced by normal human leukocytes or by normal human fibroblasts in culture.

The following examples show the preparation and testing of some of the compounds used in the invention.

EXAMPLE 1

3-(p-Chlorophenyl)-Thiazolo[3,2-a]Benzimidazole-2-Acetic Acid 3-(p-Chlorophenyl)-2,3-dihydro-3-hydroxy-thiazolo[3,2-a]-benzimidazole-2-acetic acid, (5.0 g.) is suspended in a solution of 100 ml. of a 6 N NCl and 200 ml. of dioxane. The mixture is heated at reflux for 18 hours. The solution is concentrated in vacuo to 50 ml. To the concentrate is added 200 ml. of water, and sufficient 4 N NaOH solution to dissolve all the solids. The alkaline solution is made acidic with acetic acid. The solid is collected, washed well with water and air-dried. The crude material is recrystallized from dimethoxyethane. The product (2.0 g.) melts at 242°–243° C.

Analysis for: $C_{17}H_{11}ClN_2O_2S$: Calculated: C, 59.56; H, 3.24; Cl, 10.34; N, 8.17; S, 9.36; Found: C, 59.28; H, 3.40; Cl, 11.00: N, 8.03; S, 9.93

EXAMPLE 2

To prepare: 3-phenyl-thiazolo[3,2-a]benzimidazole-2-acetic acid, treat 3-phenyl-2,3-dihydro-3-hydroxy-thiazolo[3,2-a]benzimidazole-2-acetic acid as taught in Example 1.

EXAMPLE 3

To prepare: 3-[3-(p-bromophenyl)-thiazolo[3,2-a]benzimidazole-2-yl]-propionic acid, treat 3-[3-(p-bromophenyl)-2,3-dihydro-3-hydroxythiazolo[3,2-a]benzimidazole-2-yl]-propionic acid as taught in Example 1.

EXAMPLES 4–8

Following the procedure of Example 1, there are prepared the following compounds:

| Example | Compound | Melting Point |
|---|---|---|
| 4 | 3-(p-Fluorophenyl)-thiazolo[3,2-a]-benzimidazole-2-acetic acid | 240–250° C. dec. |
| 5 | 3-(p-Bromophenyl)-thiazolo[3,2-a]-benzimidazole-2-acetic acid | 245–247° C. |
| 6 | 3-(p-Methoxyphenyl)-thiazolo[3,2-a]-benzimidazole-2-acetic acid | 275° C. dec. |
| 7 | 3-(p-Methylphenyl)-thiazolo[3,2-a]-benzimidazole-2-acetic acid | 274–280° C. dec. |
| 8 | 3-(p-Trifluoromethylphenyl)-thiazolo-[3,2-a]benzimidazole-2-acetic acid | 255–256° C. dec. |

EXAMPLE 9

The compounds used in the invention are tested for collagenase inhibition in an in vitro assay based on the procedure described by A. Sellers and J. J. Reynolds, *Biochem.J.*, 167 (1977) pp. 353–60.

Collagenase produced by normal human leukocytes or by normal human skin fibroblasts in cell cultures is purified by adsorption onto a collagen Sepharose 4B column. Prior to use in the assay, the zymogen is activated with trypsin, while the trypsin in turn, is inactivated with an excess of soybean trypsin inhibitor.

According to the assay procedure, microfuge tubes are prepared containing a total of about 150 μl. of solution containing: 25 μl collagen ($^{14}$C-acetylated collagen—2 mg/ml in 0.01% acetic acid); 25 μl. of 0.15 M tris/0.015 M CaCl$_2$, pH 7.4 75 μl. collagenase in tris buffer (0.05 M tris/0.005 M CaCl$_2$, pH 7.4); and 25 μl of collagenase inhibitor in tris buffer. Samples and controls are incubated at 35° C. for five to eighteen hours depending upon potency of the enzyme. At the end of the reaction period, the tubes are spun down in a Beckman Microfuge. A 25 μl. aliquot of each tube is then assayed in a scintillation counter. Since native collagen forms insoluble fibrils under these conditions, radioactivity detected in the supernate is a measure of collagen hydrolysis.

In a series of experiments, the compound 3-(p-Chlorophenyl)-thiazolo[3,4-a]benzimidazole-2-acetic acid is tested in the assay to determine its collagenase inhibition activity. The source of the collagenase is indicated after the experiment number. The results are summarized below.

| Experiment Number | | Concentration of compound (M) | % Collagenolysis |
|---|---|---|---|
| 1 | skin | 0 | 93 |
|   | fibroblasts | $2 \times 10^{-3}$ | 0 |
| 2 | skin | 0 | 64 |
|   | fibroblasts | $6.6 \times 10^{-5}$ | 45 |
|   |  | $2 \times 10^{-4}$ | 39 |
|   |  | $5 \times 10^{-4}$ | 27 |
|   |  | $2 \times 10^{-3}$ | 2 |
| 3 | skin | 0 | 47 |
|   | fibroblasts | $2 \times 10^{-5}$ | 38 |
| 4 | skin | 0 | 67 |
|   | fibroblasts | $5 \times 10^{-4}$ | 18 |
| 5 | skin | 0 | 54 |
|   | fibroblasts | $5 \times 10^{-4}$ | 27 |
| 6 | leukocytes | 0 | 68 |
|   |  | $5 \times 10^{-4}$ | 57 |
| 7 | skin | 0 | 70 |
|   | fibroblasts | $1 \times 10^{-4}$ | 49 |

The results show that the compound tested is able to significantly reduce collagenolysis at low levels of compound concentration.

EXAMPLE 10

The assay of Example 4 is repeated using other compounds of the invention with the following results:

| Compound | Concentration of compound (M) | % Collagenolysis |
|---|---|---|
| 3-(p-Fluorophenyl)-thiazolo[3,2-a]benzimidazole-2-acetic acid | $1 \times 10^{-3}$ | 28 |
| 3-(p-Methoxyphenyl)-thiazolo[3,2-a]benzimidazole-2-acetic acid | $1 \times 10^{-3}$ | 21 |
| 3-(p-Methylphenyl)-thiazolo[3,2-a]benzimidazole-2-acetic acid | $1 \times 10^{-3}$ | 33 |
| 3-(p-Bromophenyl)-thiazolo[3,2-a]benzimidazole-2-acetic acid | $1 \times 10^{-3}$ | 70 |
| 3-(p-Trifluoromethylphenyl)-thiazolo[3,2-a]benzimidazole-2-acetic acid | $1 \times 10^{-3}$ | 65 |

What is claimed is:

1. A method of inhibiting mammalian collagenase in mammals afflicted with a disease state in which collagen is broken down by collagenase, which comprises administering to such an afflicted mammal an amount sufficient to reverse said collagenase-induced collagen break down of a collagenase inhibitor having the formula:

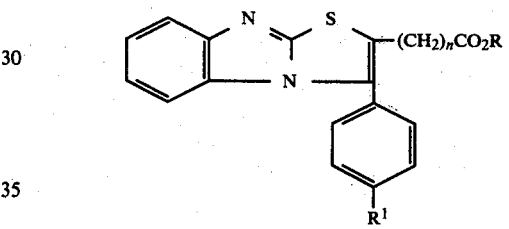

wherein R is hydrogen or lower alkyl and R$_1$ is lower alkyl, lower alkoxy, trifluoromethyl or halo, n is 1 or 2 and pharmaceutically acceptable salts thereof.

2. The method of claim 1 wherein R is hydrogen, R$_1$ is chloro and n is 1.

3. The method of claim 1, wherein R is hydrogen, R$_1$ is fluoro and n is 1.

4. The method of claim 1, wherein R is hydrogen, R$_1$ is bromo and n is 1.

5. The method of claim 1, wherein R is hydrogen, R$_1$ is methyl and n is 1.

6. The method of claim 1, wherein R is hydrogen, R$_1$ is methoxy and n is 1.

7. The method of claim 1, wherein R is hydrogen, R$_1$ is trifluoromethyl and n is 1.

* * * * *